United States Patent
Govari

(10) Patent No.: US 10,213,133 B2
(45) Date of Patent: Feb. 26, 2019

(54) MODELING OF A MAGNETIC FIELD

(71) Applicant: BIOSENSE WEBSTER (ISRAEL) LTD., Yokneam (IL)

(72) Inventor: Assaf Govari, Haifa (IL)

(73) Assignee: BIOSENSE WEBSTER (ISRAEL) LTD, Yokeam (IL)

( * ) Notice: Subject to any disclaimer, the term of this patent is extended or adjusted under 35 U.S.C. 154(b) by 1101 days.

(21) Appl. No.: 14/578,553

(22) Filed: Dec. 22, 2014

(65) Prior Publication Data

US 2016/0174872 A1    Jun. 23, 2016

(51) Int. Cl.
| | |
|---|---|
| *G01B 7/00* | (2006.01) |
| *A61B 5/06* | (2006.01) |
| *G01D 5/12* | (2006.01) |
| *G01R 33/00* | (2006.01) |
| *G01V 3/08* | (2006.01) |
| *G01V 13/00* | (2006.01) |
| *G01R 33/10* | (2006.01) |
| *A61B 34/20* | (2016.01) |

(52) U.S. Cl.
CPC .............. *A61B 5/062* (2013.01); *A61B 34/20* (2016.02); *G01B 7/003* (2013.01); *G01D 5/12* (2013.01); *G01R 33/00* (2013.01); *G01R 33/10* (2013.01); *G01V 3/08* (2013.01); *G01V 13/00* (2013.01)

(58) Field of Classification Search
CPC ........ A61B 5/062; A61B 34/20; G01B 7/003; G01D 5/12; G01R 33/00
See application file for complete search history.

(56) References Cited

U.S. PATENT DOCUMENTS

| 6,484,118 | B1 | 11/2002 | Govari | |
| 7,809,421 | B1 | 10/2010 | Govari | |
| 2007/0035298 | A1* | 2/2007 | Pittaluga | G01R 33/387 |
| | | | | 324/309 |
| 2010/0312089 | A1 | 12/2010 | Wright et al. | |
| 2011/0238399 | A1 | 9/2011 | Ophir et al. | |
| 2011/0240044 | A1* | 10/2011 | Duan | A61B 1/00158 |
| | | | | 128/899 |
| 2013/0226516 | A1* | 8/2013 | Jeon | G01R 33/0064 |
| | | | | 702/158 |
| 2014/0018662 | A1 | 1/2014 | Montag | |

OTHER PUBLICATIONS

Hawley, J. Magnetic Field in and Around a Finite Cylindrical Air-Core Solenoid. Paper, Sep. 2011.
EP 15201712.5—European Search Report dated Jun. 29, 2016.

* cited by examiner

*Primary Examiner* — Jermele M Hollington
*Assistant Examiner* — Feba Pothen
(74) *Attorney, Agent, or Firm* — Louis J. Capezzuto

(57) ABSTRACT

A method, including generating a magnetic field in a region from a first magnetic field radiator located at a first position and a second magnetic field radiator located at a second position. A volume having a multiplicity of vertices is delineated within the region, and respective values of the magnetic field at the multiplicity of vertices are measured. In response to the respective values, respective first dipole moments to the first magnetic field radiator and respective second dipole moments to the second magnetic field radiator are assigned. A value of the magnetic field within the volume is calculated in terms of the first dipole moments and the second dipole moments.

28 Claims, 3 Drawing Sheets

MODELING OF A MAGNETIC FIELD

FIELD OF THE INVENTION

The present invention relates generally to magnetic field generation, and specifically to modeling of the generated field.

BACKGROUND OF THE INVENTION

A wide range of medical procedures involve placing objects, such as sensors, tubes, catheters, dispensing devices, and implants, within the body. Real-time imaging methods are often used to assist doctors in visualizing the object and its surroundings during these procedures. Some methods track the objects using magnetic fields. However, disturbances in the magnetic field may create errors in the tracking.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention provides a method, including:

generating a magnetic field in a region from a first magnetic field radiator located at a first position and a second magnetic field radiator located at a second position;

delineating within the region a volume having a multiplicity of vertices;

measuring respective values of the magnetic field at the multiplicity of vertices;

in response to the respective values, assigning respective first dipole moments to the first magnetic field radiator and assigning respective second dipole moments to the second magnetic field radiator; and calculating a value of the magnetic field within the volume in terms of the first dipole moments and the second dipole moments.

The method typically includes, subsequent to calculating the value, inserting into the region a probe, configured to measure the value of the magnetic field, and determining a location of the probe within the region in response to the measured value.

In a disclosed embodiment the volume is a cube having eight vertices.

In a further disclosed embodiment calculating the value of the magnetic field includes the first and second magnetic radiators operating as simple dipoles having poles obeying an inverse square law.

The method may further include assigning the respective first dipole moments to the first magnetic field radiator and assigning the respective second dipole moments to the second magnetic field radiator in response to displacements of the multiplicity of vertices from an origin of a frame of reference defined by the first position and the second position.

In an alternative embodiment the value of the magnetic field for a point within the volume is calculated in terms of a first average of the first dipole moments assigned for the multiplicity of vertices and of a second average of the second dipole moments assigned for the multiplicity of vertices. Typically the first and second averages are respective linear weighted averages calculated in terms of a location of the point within the volume.

In a further alternative embodiment the first magnetic field radiator and the second magnetic field radiator respectively transmit a first alternating magnetic field at a first frequency and a second alternating magnetic field at a second frequency different from the first frequency.

There is further provided, according to an embodiment of the present invention apparatus, including:

a first magnetic field radiator located at a first position and a second magnetic field radiator located at a second position, the radiators being configured to generate a magnetic field in a region; and a processor, configured to:

delineate within the region a volume having a multiplicity of vertices, measure respective values of the magnetic field at the multiplicity of vertices, in response to the respective values, assign respective first dipole moments to the first magnetic field radiator and assign respective second dipole moments to the second magnetic field radiator, and calculate a value of the magnetic field within the volume in terms of the first dipole moments and the second dipole moments.

The present disclosure will be more fully understood from the following detailed description of the embodiments thereof, taken together with the drawings, in which:

DETAILED DESCRIPTION OF EMBODIMENTS

Overview

Prior art systems for modeling fields in a region transmitted into by magnetic field radiators use mathematical procedures, such as spherical harmonics, that are computationally heavy. The mathematical procedures are necessary to account for the radiators in practice not behaving as simple dipole radiators, and the procedures compensate for deviations from a simple dipole model for the radiators.

Embodiments of the present invention take a different approach, and assume a model where the radiators do behave as simple dipole radiators. However, the dipole moment assumed for a given radiator is assumed to be a function of a location within the region. Using this model leads to simplified computation, with no reduction in accuracy of the field predicted by the model compared with prior art systems of modeling.

Thus, for a volume in the region having a multiplicity of vertices, the magnetic field from a plurality of radiators is measured at each of the vertices. For a given radiator, a respective dipole moment for the radiator is assigned to each of the vertices. A value of the magnetic field at a point within the volume is calculated in terms of the respective dipole moments of each of the vertices of the volume. The calculation is made by finding an average, typically a linear weighted average, of the dipole moments assigned for the multiplicity of vertices.

The inventor has found that applying the calculation to contiguous volumes filling the region provides an efficient, fast, and accurate method for modeling the magnetic field in the region. Furthermore, the calculation leads to the modeled magnetic field being continuous over the whole region, while not necessarily being differentiable at volume boundaries.

System Description

Figure 1:
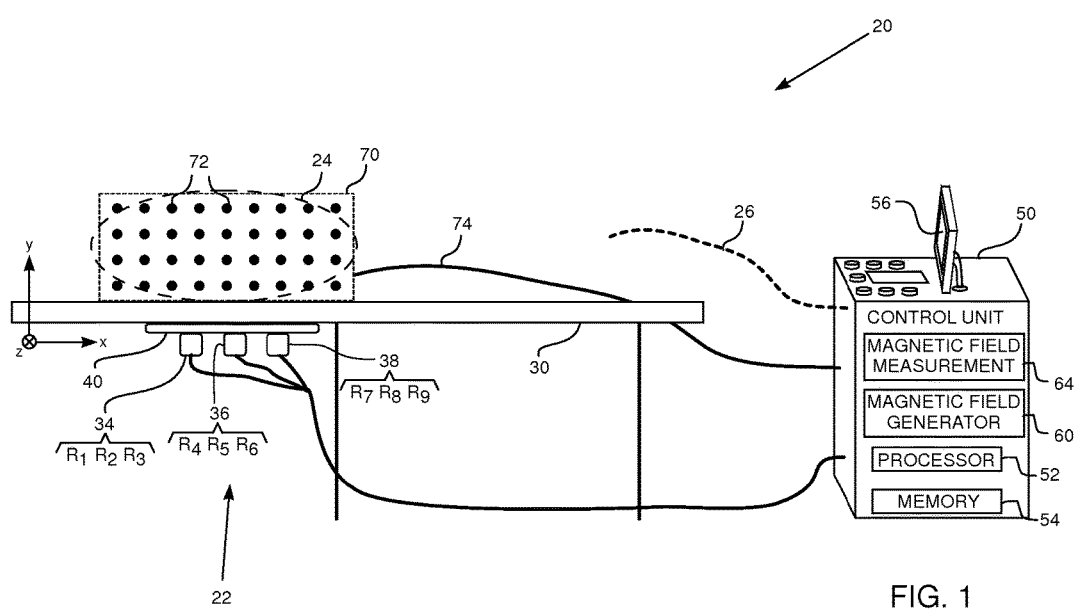
FIG. 1 is a schematic, pictorial illustration of a magnetic field modeling system, according to an embodiment of the present invention.

Reference is now made to FIG. 1, which is a schematic, pictorial illustration of a magnetic field modeling system 20, according to an embodiment of the present invention. System 20 produces a model of the magnetic field generated by a plurality of generally similar alternating magnetic field radiators 22 transmitting into a region 24. Region 24 is schematically represented by an ellipse in the figure.

Typically, once the field has been modeled by system 20, a patient is placed in the field. A catheter probe 26 is inserted into an organ of the patient by a medical professional, and the magnetic field at the probe is measured. (For clarity, probe 26 is shown in FIG. 1 with broken lines.) The measured value is compared with values of the field derived the model, and the comparison determines the position and orientation of the probe within the patient's organ. The patient typically lies (with their organ within region 24) on an operating table during a procedure performed by the medical professional. For clarity and simplicity, neither the patient nor the medical professional are shown in FIG. 1.

In embodiments of the present invention there are p radiators 22, where p is an integer greater than one. Radiators 22 are also referred to herein as $R_1, R_2, \ldots R_n, \ldots R_p$, where $1 < n \leq p$ and n is an integer. The radiators are fixed with respect to table 30, and the fixed radiators define a radiator frame of reference, having an orthogonal set of xyz axes. As stated above, radiators 22 transmit alternating magnetic fields into region, and radiators $R_1, R_2, \ldots R_n, \ldots R_p$, are assumed to radiate at respective frequencies $f_1, f_2, \ldots f_n, \ldots f_p$.

In one embodiment the radiators are assumed to be grouped into three radiator sets 34, 36, and 38 fixed to a location pad 40, which is in turn fixed to the table. Each set comprises three triaxial coils, which are orthogonal to each other and which act as three magnetic field radiators. Thus set 34 comprises radiators $R_1, R_2, R_3$, set 36 comprises radiators $R_4, R_5, R_6$, and set 38 comprises radiators $R_7, R_8, R_9$. U.S. Pat. No. 6,484,118, to Govari, whose disclosure is incorporated herein by reference, describes such an arrangement of coils used as magnetic field radiators. By way of example, the xyz axes of the radiator frame of reference is assumed to have its origin in location pad 40, and the z axis is assumed to be perpendicular to the location pad. (For clarity, FIG. 1 shows the xyz axes separated from the location pad.)

However, it will be understood that the arrangement of nine radiators assumed above is by way of example, so that other embodiments of the present invention have other numbers and/or arrangements of radiators. U.S. Pat. No. 6,484,118, referenced above, describes other arrangements of radiators. In an operating environment where magnetic fields from the radiators distort, such as in a magnetic resonance imaging (MRI) facility, a disclosed embodiment uses 15 radiators.

A control unit 50 operates system 20. Control unit includes a processor 52, typically a computer with appropriate signal processing circuits. Unit 50 comprises a magnetic field generator module 60, which processor 52 uses to drive radiators 22. The control unit also comprises a magnetic field measurement module 64, which is configured to receive signals from one or more probes positioned in the field generated by radiators 22, and to evaluate, typically together with processor 52, the field at the one or more probes. The processor uses a memory 54, which typically comprises both volatile and non-volatile data storage devices, wherein data for operating system 20 is stored. The processor is typically coupled to provide a visual display 56 to an operator of system 20.

Typically, processor 52 is programmed in software to carry out the functions described herein. The software may be downloaded to the processor in electronic form, over a network, for example, or it may, alternatively or additionally, be provided and/or stored on non-transitory tangible media, such as magnetic, optical, or electronic memory.

System 20 also comprises apparatus which is able to measure the magnetic fields that are transmitted by radiators 22 into region 24. In one embodiment of the present invention, a mapper 70 is used to measure the magnetic fields, the mapper comprising an array of q magnetic field detectors 72 which are fixedly mounted in known positions on solid bases, such as sheets of plastic. Mapper 70 is configured so that it may be positioned on table 30 in a known predetermined position and orientation relative to location pad 40. In one embodiment, detectors 72 are arranged so that they are at the vertices of cubical volumes that fill region 24. In one embodiment the edges of the cubical volumes are 2 cm long, so that the vertices are separated by 2 cm. However, any other convenient length of the edges may be used.

Detectors 72 may comprise any convenient sensors for measuring the magnitude and direction of an alternating magnetic field, such as Hall probes or one or more coils. The signals from the detectors are transferred to module 64, typically by a cable 74, although any other convenient transfer method may be used, such as wireless transmission. Module 64 and/or processor 52 uses the signals to measure the field at the detectors.

Field measuring systems that are an alternative to mapper 70 will be apparent to those having ordinary skill in the art. For example instead of an array of detectors 72, one or more detectors substantially the same as detectors 72 may be mounted on a jig that is configured to translate by known distances in three dimensions, and the measurements of the field are made as the one or more detectors traverse region 24. Other such systems, that are evident to one having ordinary skill in the art, are assumed to be comprised within the scope of the present invention.

As described in more detail below, mapper 70 may be used in a calibration phase of system 20. The mapper and its cable are removed when system 20 is in an operational phase.

Figure 2:
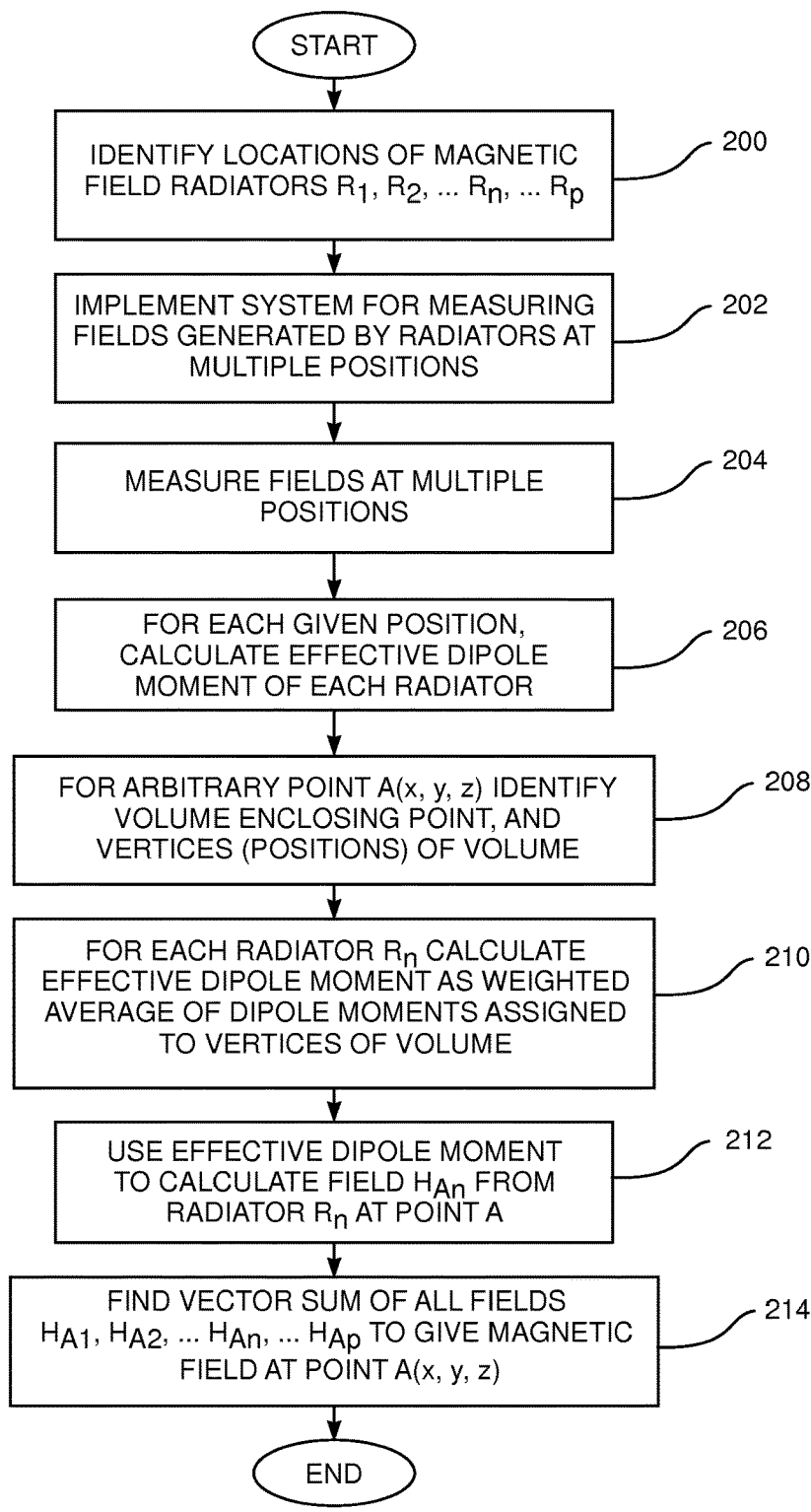
FIG. 2 is a flowchart of steps describing the production of the model formed by the system of FIG. 1, according to an embodiment of the present invention.
Figure 3:
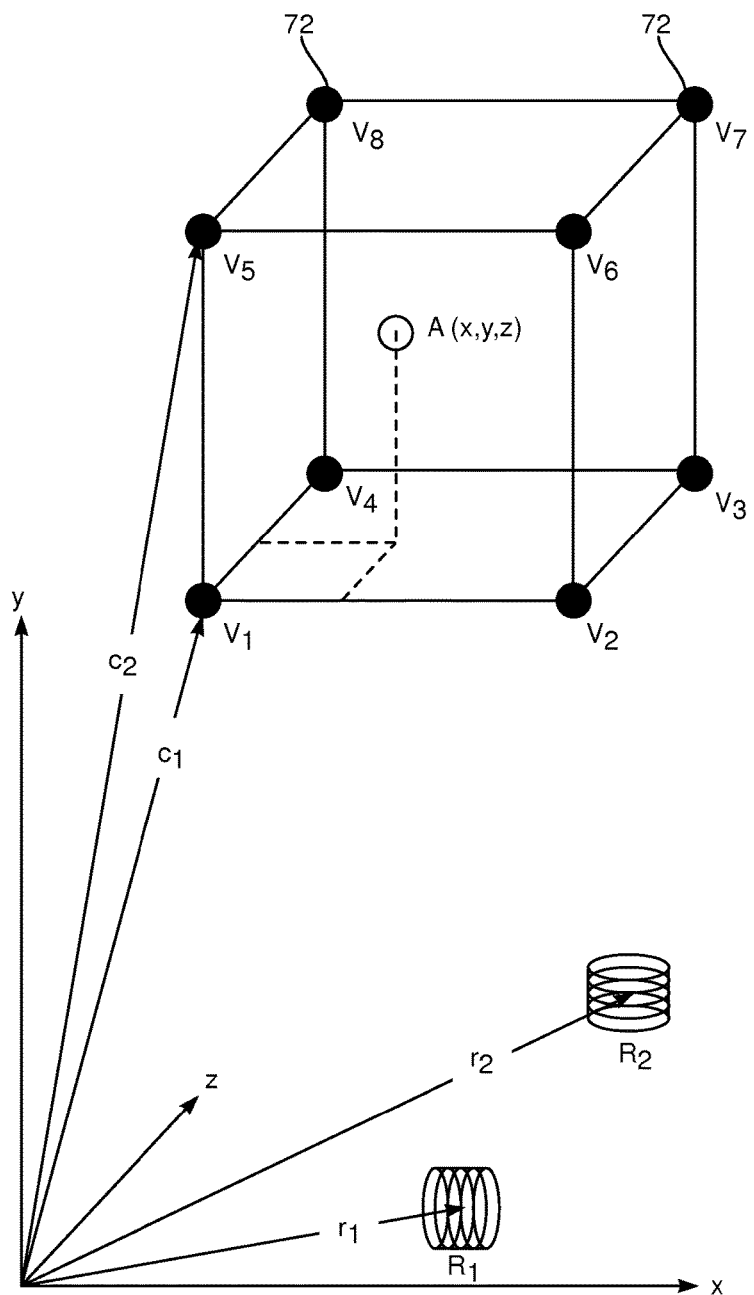
FIG. 3 is a schematic diagram illustrating the steps, according to an embodiment of the present invention.

FIG. 2 is a flowchart of steps describing the production of the model formed by system 20, and FIG. 3 is a schematic diagram illustrating the steps, according to an embodiment of the present invention. In an initial step 200, radiators 22 are fixed in position, and the locations of each of the radiators $R_1, R_2, \ldots R_n, \ldots R_p$ are measured. FIG. 3 illustrates locations of two radiators $R_1, R_2$, having respective location vectors $r_1, r_2$.

In an assembly step 202, a system for measuring the fields, generated by radiators 22, in known locations in region 24, is set up. For clarity, in the description herein the system set up is assumed to comprise mapper 70, with detectors 72 arranged at the vertices of cubes. FIG. 3 illustrates one cube having eight cube vertices, $V_1, V_2, \ldots V_8$, which are assumed to have respective location vectors $c_1, c_2, \ldots c_8$. For the q detectors of mapper 70, there are q vertices $V_1, V_2, \ldots V_q$ each having a location vector $c_1, c_2, \ldots c_q$. In the following description, a generic vertex in region 24 is assumed to have a location vector $c_m$, where m is an index, and the vertices may also be referred to herein by their location vectors.

In a measurement step 204, radiators 22 are activated and the magnitude and direction of the respective field from each radiator 22 is measured by each detector 72. Thus, if there are nine radiators, each detector measures nine magnitudes and nine directions for the field from the radiators. In general each of the q detectors measures p magnitudes and p directions of the fields from the p radiators.

In a calculation step 206, for each vertex, processor 52 calculates a respective effective dipole moment for each radiator $R_n$. The calculation assumes that each radiator is a simple dipole which has a dipole field equation derived from an inverse square law which magnetic poles of the dipole obey. The simple dipole field equation is given by equation (1):

$$H(r) = \frac{1}{4\pi}\left(\frac{3r(m \cdot r)}{|r|^5} - \frac{m}{|r|^3}\right) \quad (5)$$

where m is the dipole moment of the radiator,
r is the displacement of a point from the radiator.
and H is the field generated by the radiator at the point. H, m, and r are vectors.

For a radiator $R_n$, radiating at a frequency $f_n$ to a vertex $c_m$, and where the vertex has a displacement $r_{nm}$ from the radiator, equation (1) may be rewritten:

$$H_{nm} = f(m_{nm}, r_{nm}) \quad (2)$$

where $m_{nm}$ is the effective dipole moment of radiator $R_n$ at vertex $c_m$,
$r_{nm}$ is the displacement of vertex $c_m$ from the radiator,
$H_{nm}$ is the field generated by the radiator at the vertex, and
f is a function given by equation (1).

Equation (2) may be rewritten as equation (3):

$$m_{nm} = g(H_{nm}, r_{nm}) \quad (3)$$

where $m_{nm}$, $H_{nm}$, $r_{nm}$ are defined above with reference to equation (2), and
g is a function derived from function f.

Thus, in step 206, the processor uses equation (3) to calculate, for each vertex $c_m$, respective effective dipole moments $m_{nm}$ for each radiator $R_n$. The processor stores the dipole moment values for use in the remaining steps of the flowchart.

Step 206 is the concluding step of a calibration phase of the modeling system 20, wherein the magnetic field from radiators $R_n$ has been determined for the calibration vertices located in region 24. The following steps of the flowchart build on the results found in step 206 and describe an interpolation process to find an expression for the magnetic field at any point in region 24.

In an identification step 208, the vertices of the cube in which an arbitrary point A(x, y, z) is located are identified. Referring to FIG. 3, point A is assumed to be in a cube having vertices $V_1, V_2, \ldots V_8$.

In the following description, the origin of coordinates of the xyz axes is assumed to be have been translated from its initial origin to an origin at vertex $V_1$, and the cube edges are assumed to define the directions of the axes. It will be understood that the translation is by a known amount. In addition, the cube edge is assumed to have a nominal length of 1. In this case, the coordinates of point A have the property: $0 \leq x,y,z \leq 1$. The above assumptions simplify the following description, but it will be understood that embodiments of the present invention place no limitations on the axes used to define the vertices of the cubes, or on the lengths of the cube edges. (For clarity the translation of the axes to vertex $V_1$ is not shown in FIG. 3.)

In a first dipole moment step 210, the processor recalls the effective dipole moments of a selected radiator $R_n$, for each of the vertices of the cube. In this case the dipole moments are $m_{n1}, m_{n2}, m_{n3}, \ldots m_{n8}$.

The processor then calculates, as an effective dipole moment for point A, an average of the respective effective dipole moments of the vertices surrounding point A. In a disclosed embodiment described herein, the average is a linear weighted average, but it will be understood that other averages, including even a simple average, are included in the scope of the present invention.

Equation (4) applies for the linear weighted average:

$$m_n^A = m_{n1}(1-x)(1-y)(1-z) + m_{n2}(x)(1-y)(1-z) + m_{n3}(1-x)(y)(1-z) + m_{n4}(x)(y)(1-z) + m_{n5}(1-x)(1-y)(z) + m_{n6}(x)(1-y)(z) + m_{n7}(1-x)(y)(z) + m_{n8}(x)(y)(z) \quad (4)$$

where $m_n^A$ is the effective dipole moment of Radiator $R_n$ for point A(x, y, z) in the cube having vertices $V_1, V_2, \ldots V_8$.

The processor uses equation (4) to calculate an effective dipole moment to be used at point A(x,y,z) for each of the p radiators $R_1, \ldots, R_p$, thus finding p effective dipole moments.

In a second dipole moment step 212, the processor uses the p effective dipole moments evaluated in step 210 to calculate the p respective fields generated from radiators $R_1, \ldots R_p$ at point A(x,y,z). Each of the fields is calculated using equation (5), which is an adaptation of equation (1):

$$H_{An}(r_A) = \frac{1}{4\pi}\left(\frac{3r(m_n^A \cdot r_A)}{|r_A|^5} - \frac{m_n^A}{|r_A|^3}\right) \quad (5)$$

where $r_A$ is a vector from the initial origin of coordinates to point A,
$H_{An}(r_A)$ is the vector field from radiator $R_n$ at point A, and
$m_n^A$ is defined with reference to equation (4).

In a final summation step 214, the processor sums vectorially all the p fields $H_{A1}(r_A), \ldots H_{An}(r_A), \ldots H_{Ap}(r_A)$ calculated from the applications of equation (5), according to equation (6):

$$H(r_A) = H_{A1}(r_A) + \ldots + H_{An}(r_A) + \ldots + H_{Ap}(r_A) \quad (6)$$

where $H(r_A)$ is the overall magnetic field from all radiators $R_1, \ldots R_p$ at point A(x,y,z).

Returning to FIG. 1, once the procedure of the flowchart of FIG. 2 has been performed, the magnetic field has been modeled for all of region 24. A patient may be placed so that a portion of the patient to be investigated is in region 24, and probe 26 may be inserted into the patient, in the region.

The probe, together with magnetic field measurement module 64, measures values of all the different vectors of the magnetic fields comprised in $H(r_A)$ (equation (6)), using the property that each of the vector components is transmitted at a different frequency. From a knowledge of the values of all the different components, and from the modeling of the values of the components derived from equation (5), processor 52 derives the position, i.e., the location and the orientation of probe 26.

While the description above assumes that detectors 72 are at the vertices of cubes, it will be understood that the detectors may be arranged to be at the vertices of other solid volumes, such as tetrahedra. While the solid volumes are typically of the same type, for ease of computation, there is no necessity for this limitation, so that, for example, the detectors may be assumed to be at the vertices of a mixture of cubes and tetrahedral. Thus, the vertices corresponding to detectors 72 may be vertices of any combination of solid volumes that fill region 24. Such a combination typically necessitates one or more different equations than equation (4), to derive the weighted average for the different volumes, but the changes needed to the equation will be apparent to one having ordinary skill in the art.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

I claim:

1. A method, comprising:
generating a magnetic field in a region from a first magnetic field radiator located at a first position and a second magnetic field radiator located at a second position;
delineating within the region a volume having a multiplicity of vertices;
measuring respective values of the magnetic field at the multiplicity of vertices;
in response to the respective values and in response to displacements of the multiplicity of vertices from an origin of a frame of reference defined by the first position and the second position, assigning respective first dipole moments to the first magnetic field radiator and assigning respective second dipole moments to the second magnetic field radiator; and
calculating a value of the magnetic field within the volume in terms of the first dipole moments and the second dipole moments.

2. The method according to claim 1, and comprising, subsequent to calculating the value, inserting into the region a probe, configured to measure the value of the magnetic field, and determining a location of the probe within the region in response to the measured value.

3. The method according to claim 1, wherein the volume is a cube having eight vertices.

4. The method according to claim 1, wherein calculating the value of the magnetic field comprises the first and second magnetic radiators operating as simple dipoles having poles obeying an inverse square law.

5. The method according to claim 1, wherein the value of the magnetic field for a point within the volume is calculated in terms of a first average of the first dipole moments assigned for the multiplicity of vertices and of a second average of the second dipole moments assigned for the multiplicity of vertices.

6. The method according to claim 5, wherein the first and second averages are respective linear weighted averages calculated in terms of a location of the point within the volume.

7. The method according to claim 1, wherein the first magnetic field radiator and the second magnetic field radiator respectively transmit a first alternating magnetic field at a first frequency and a second alternating magnetic field at a second frequency different from the first frequency.

8. An apparatus, comprising:
a first magnetic field radiator located at a first position and a second magnetic field radiator located at a second position, the radiators being configured to generate a magnetic field in a region; and
a processor, configured to:
delineate within the region a volume having a multiplicity of vertices,
measure respective values of the magnetic field at the multiplicity of vertices,
in response to the respective values and in response to displacements of the multiplicity of vertices from an origin of a frame of reference defined by the first position and the second position, assign respective first dipole moments to the first magnetic field radiator and assign respective second dipole moments to the second magnetic field radiator, and
calculate a value of the magnetic field within the volume in terms of the first dipole moments and the second dipole moments.

9. The apparatus according to claim 8, and comprising a probe that is inserted into the region subsequent to calculating the value, and wherein the probe is configured to measure the value of the magnetic field, and wherein the processor is configured to determine a location of the probe within the region in response to the measured value.

10. The apparatus according to claim 8, wherein the volume is a cube having eight vertices.

11. The apparatus according to claim 8, wherein the first and second magnetic radiators operate as simple dipoles having poles obeying an inverse square law.

12. The apparatus according to claim 8, wherein the value of the magnetic field for a point within the volume is calculated in terms of a first average of the first dipole moments assigned for the multiplicity of vertices and of a second average of the second dipole moments assigned for the multiplicity of vertices.

13. The apparatus according to claim 12, wherein the first and second averages are respective linear weighted averages calculated in terms of a location of the point within the volume.

14. The apparatus according to claim 8, wherein the first magnetic field radiator and the second magnetic field radiator respectively transmit a first alternating magnetic field at a first frequency and a second alternating magnetic field at a second frequency different from the first frequency.

15. A method, comprising:
generating a magnetic field in a region from a first magnetic field radiator located at a first position and a second magnetic field radiator located at a second position;
delineating within the region a volume having a multiplicity of vertices;
measuring respective values of the magnetic field at the multiplicity of vertices;
in response to the respective values, assigning respective first dipole moments to the first magnetic field radiator and assigning respective second dipole moments to the second magnetic field radiator; and calculating a value of the magnetic field within the volume in terms of the first dipole moments and the second dipole moments;

wherein the value of the magnetic field for a point within the volume is calculated in terms of a first average of the first dipole moments assigned for the multiplicity of vertices and of a second average of the second dipole moments assigned for the multiplicity of vertices.

16. The method according to claim 15, and comprising, subsequent to calculating the value, inserting into the region a probe, configured to measure the value of the magnetic field, and determining a location of the probe within the region in response to the measured value.

17. The method according to claim 15, wherein the volume is a cube having eight vertices.

18. The method according to claim 15, wherein calculating the value of the magnetic field comprises the first and second magnetic radiators operating as simple dipoles having poles obeying an inverse square law.

19. The method according to claim 15, and comprising assigning the respective first dipole moments to the first magnetic field radiator and assigning the respective second dipole moments to the second magnetic field radiator in response to displacements of the multiplicity of vertices from an origin of a frame of reference defined by the first position and the second position.

20. The method according to claim 15, wherein the first and second averages are respective linear weighted averages calculated in terms of a location of the point within the volume.

21. The method according to claim 15, wherein the first magnetic field radiator and the second magnetic field radiator respectively transmit a first alternating magnetic field at a first frequency and a second alternating magnetic field at a second frequency different from the first frequency.

22. An Apparatus, comprising:
a first magnetic field radiator located at a first position and a second magnetic field radiator located at a second position, the radiators being configured to generate a magnetic field in a region; and a processor, configured to:
delineate within the region a volume having a multiplicity of vertices,
measure respective values of the magnetic field at the multiplicity of vertices,
in response to the respective values, assign respective first dipole moments to the first magnetic field radiator and assign respective second dipole moments to the second magnetic field radiator, and
calculate a value of the magnetic field within the volume in terms of the first dipole moments and the second dipole moments;
wherein the value of the magnetic field for a point within the volume is calculated in terms of a first average of the first dipole moments assigned for the multiplicity of vertices and of a second average of the second dipole moments assigned for the multiplicity of vertices.

23. The apparatus according to claim 22, and comprising a probe that is inserted into the region subsequent to calculating the value, and wherein the probe is configured to measure the value of the magnetic field, and wherein the processor is configured to determine a location of the probe within the region in response to the measured value.

24. The apparatus according to claim 22, wherein the volume is a cube having eight vertices.

25. The apparatus according to claim 22, wherein the first and second magnetic radiators operate as simple dipoles having poles obeying an inverse square law.

26. The apparatus according to claim 22, wherein the processor is configured to assign the respective first dipole moments to the first magnetic field radiator and assign the respective second dipole moments to the second magnetic field radiator in response to displacements of the multiplicity of vertices from an origin of a frame of reference defined by the first position and the second position.

27. The apparatus according to claim 22, wherein the first and second averages are respective linear weighted averages calculated in terms of a location of the point within the volume.

28. The apparatus according to claim 8, wherein the first magnetic field radiator and the second magnetic field radiator respectively transmit a first alternating magnetic field at a first frequency and a second alternating magnetic field at a second frequency different from the first frequency.

* * * * *